(12) United States Patent
Tabor

(10) Patent No.: US 8,753,269 B2
(45) Date of Patent: Jun. 17, 2014

(54) MINIMALLY INVASIVE ACCESS DEVICE FOR HEART VALVE PROCEDURES

(75) Inventor: Charles Tabor, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 799 days.

(21) Appl. No.: 12/715,516

(22) Filed: Mar. 2, 2010

(65) Prior Publication Data

US 2010/0274096 A1 Oct. 28, 2010

Related U.S. Application Data

(60) Provisional application No. 61/171,887, filed on Apr. 23, 2009.

(51) Int. Cl.
*A61B 1/32* (2006.01)

(52) U.S. Cl.
USPC .......................................... 600/210; 600/201

(58) Field of Classification Search
USPC .................. 600/201–249; 604/164.1, 164.11; 606/108; 433/93, 140
See application file for complete search history.

(56) References Cited

U.S. PATENT DOCUMENTS

| 4,067,331 | A | * | 1/1978 | Berman | 128/200.26 |
| 5,906,577 | A | * | 5/1999 | Beane et al. | 600/207 |
| 6,500,002 | B2 | * | 12/2002 | Horiguchi | 433/140 |
| 6,648,819 | B2 | * | 11/2003 | Lee | 600/236 |
| 2004/0005529 | A1 | * | 1/2004 | O'Neill | 433/140 |
| 2005/0214713 | A1 | * | 9/2005 | O'Neill | 433/140 |
| 2006/0287583 | A1 | * | 12/2006 | Mangiardi | 600/208 |
| 2007/0225568 | A1 | * | 9/2007 | Colleran | 600/201 |
| 2008/0287743 | A1 | * | 11/2008 | Smith et al. | 600/201 |

FOREIGN PATENT DOCUMENTS

| WO | 96/24300 | | 8/1996 | | |
| WO | WO 9624300 | * | 8/1996 | ............. | A61B 17/34 |
| WO | WO 9624300 A1 | * | 8/1996 | ............. | A61B 17/34 |
| WO | 2008/066543 | | 6/2008 | | |

* cited by examiner

*Primary Examiner* — Matthew Lawson
*Assistant Examiner* — Si Ming Lee

(57) ABSTRACT

A surgical access device including a lower portion having a central opening spaced from a lower portion outer wall, an upper portion adjacent to the lower portion and having a central opening spaced from an upper portion outer wall, and at least one flange portion extending outwardly from the upper and lower portions. The device can further include a gap extending from the central openings of the lower and upper portions and through their outer walls.

10 Claims, 2 Drawing Sheets

MINIMALLY INVASIVE ACCESS DEVICE FOR HEART VALVE PROCEDURES

CROSS-REFERENCE TO RELATED APPLICATION

This application claims the benefit under 35 U.S.C. §119 (e) of U.S. Provisional Patent Application No. 61/171,887, filed Apr. 23, 2009, which is incorporated herein by reference in its entirety.

TECHNICAL FIELD

The present invention relates generally to devices for use in surgical procedures and more specifically relates to devices for use in minimally invasive heart valve surgical procedures.

BACKGROUND

One general type of heart valve surgery involves an open-heart surgical procedure that is conducted under general anesthesia, during which the heart is stopped and blood flow is controlled by a heart-lung bypass machine. Such open-heart procedures typically require exposure of the heart and its vessels through median sternotomy (dividing the breastbone), which is considered one of the most invasive and traumatic aspects of open-heart surgery. This type of valve surgery is highly invasive and exposes the patient to a number of potential risks, such as infection, stroke, renal failure, and adverse effects associated with use of the heart-lung machine, for example.

Due to the drawbacks of open-heart surgical procedures, there has been an increased interest in minimally invasive surgical techniques. Such minimally invasive approaches allow access to the heart through relatively small incisions and without stopping the heart. In addition, minimally invasive techniques do not require separation of the breastbone (sternum) and ribcage, and do not require use of a heart-lung machine. Other benefits of minimally invasive heart surgery can include a smaller incision site for the patient and a smaller resultant scar, along with a decreased risk of infection, less bleeding, less trauma, a decreased length of stay in the hospital, and a shorter recovery time. Although some devices and methods are available for allowing such minimally invasive access, it is desirable to provide additional devices and methods for accessing specific areas of the heart that can accommodate particular requirements and/or preferences of the surgeon.

BRIEF DESCRIPTION OF THE DRAWINGS

The present invention will be further explained with reference to the appended Figures, wherein like structure is referred to by like numerals throughout the several views, and wherein.

SUMMARY

Figure 1:
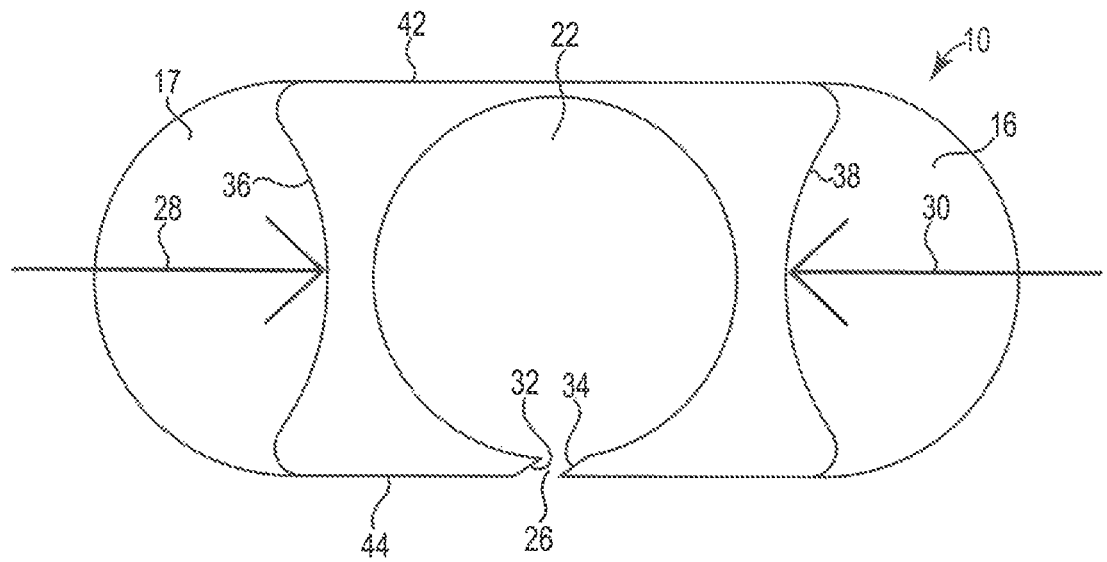
FIG. 1 is top view of a device of the invention for accessing a heart valve area of a patient.

The invention provides a mechanism that allows relatively easy access to locations of the heart, such as the aorta, for performing surgical procedures within a certain access area. This is accomplished with a device that includes a central core area having an internal access opening or port extending through its length and flanges that extend from the central area. The device is deformable in at least one dimension by applying forces that temporarily reconfigure or compress the central core area of the device. The device can then be allowed to expand back to its original configuration by removing those compressive or reconfiguring forces. In particular, the device can be compressed for insertion into an opening created by an incision in the skin of a patient so that the flanges are positioned beneath a layer of skin, and then allowed to expand after it is properly positioned. The outer diameter of the central area in its expanded condition can be sufficient to engage with the inner wall of the vessel at the incision site, while the inner diameter of the central area is sized to provide sufficient space for a surgeon to manipulate instruments while accessing internal organs.

In one embodiment of the invention, an access device is provided. The device generally includes a lower portion, an upper portion adjacent to the lower portion and positioned along the same longitudinal axis as the lower portion, and at least one flange positioned generally between the upper and lower portions and extending outwardly relative to the longitudinal axis. The device further includes an access port or opening extending through its height, and a slot or gap that extends generally along the height of the device. The slot or gap allows for reconfiguration or compression of the central area of the device in order to make it smaller or differently shaped for positioning relative to an incision. The upper portion of the device also includes gripping surfaces that can be used to grasp and compress portions of the device. In one particular embodiment, the device includes two flanges and the upper portion includes two concave gripping surfaces positioned on generally opposite sides of the device.

In another embodiment of the invention, a method is provided of inserting an access device of the type described above within an area adjacent to an incision in the skin of a patient. The method includes the steps of compressing the device, such as by pressing two gripping surfaces on opposite sides of the device toward each other, and then rotating the device so that its longitudinal axis is angled relative to its desired final orientation. The device can then be moved into the opening created by the incision, and once it is sufficiently inserted into the opening, it can be rotated to its desired orientation. In particular, the device can be rotated so that its flanges are positioned below the skin and its upper portion is positioned to allow access to its internal area from outside the body. In one particular embodiment, the device is used to allow access to the aortic region of a patient, wherein an incision is made in the area generally above the aorta so that the device is positioned with its access opening immediately adjacent to the aorta. Once the device is generally in its desired location, the compressive forces can be removed to allow the device to expand toward its original configuration.

DETAILED DESCRIPTION

Figure 2:
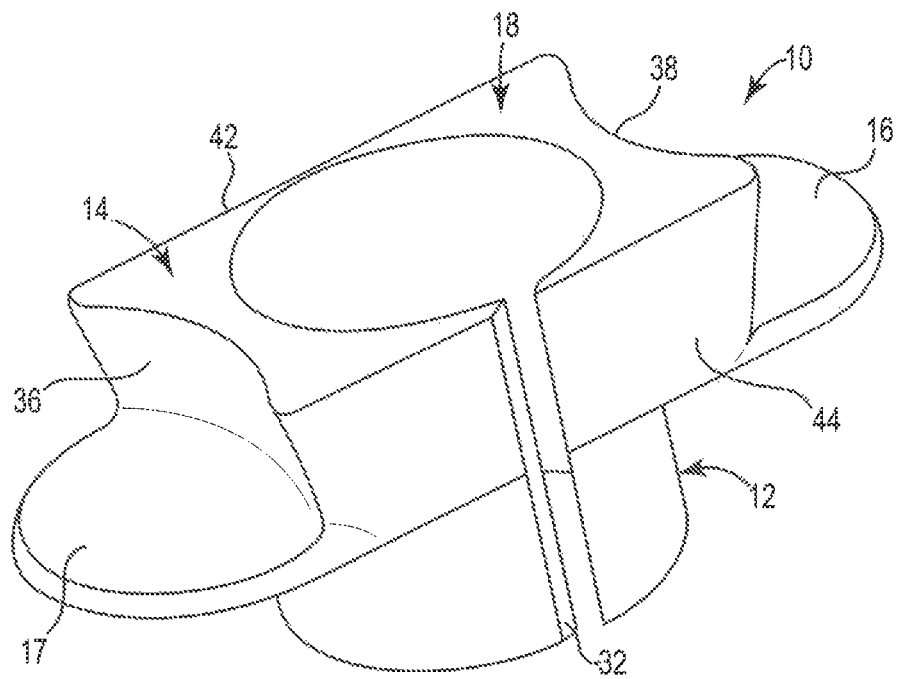
FIG. 2 is a perspective view of the device of FIG. 1.

Referring now to the Figures, wherein the components are labeled with like numerals throughout the several Figures, and initially to FIGS. 1 and 2, a device 10 that can be used to provide access to an aorta in accordance with the invention is illustrated. While the device 10 is described herein as being used for aortic access, it can also be used in other areas of the body that are situated in such a way that access to certain internal organs or areas would be possible from outside the body using this device. In one embodiment, device 10 can be used to assist a surgeon in minimal access aortic valve procedures by maintaining an uninhibited access port through which surgical procedures can be performed. As described herein, the device 10 can be referred to as a surgical access device that can be used for a wide variety of procedures, such as transcatheter aortic valve procedures, including transapical valve replacements, for example.

Device 10 includes a cylindrical lower portion 12, an upper portion 14, and two flange portions 16, 17 that extend outwardly from the general area where the lower portion 12 and upper portion 14 meet. As shown, the flange portions 16, 17 are positioned to extend in opposite directions on generally opposite sides of the lower and upper portions 12, 14. However, the device may instead include more or less flange portions and/or the flange portions can be positioned such that they are not directly opposite each other relative to the central area of the device.

The lower portion 12 has an opening or port through its center and its outer profile can be generally cylindrical with generally parallel outer sidewalls, as shown, or can instead have walls that are at least somewhat angled or tapered relative to each other. Alternatively, the lower portion can include an outer profile that is elliptical, rectangular, triangular, or otherwise shaped to accommodate certain surgical instruments and/or particular body access locations. The opening or port can have the same shape as the outer profile of the lower portion, or the shape of the opening or port can be somewhat or substantially different than the outer profile of the lower portion. For one example, it may be desirable for the lower portion to have a generally rectangular outer profile while the opening or port can have a cylindrical shape.

The upper portion 14 has an opening or port through its center and an outer profile that includes walls that are angled from the flange portions 16, 17 toward an upper end 18 of the device 10, as shown. The angles of the walls can be generally similar to that shown, or can have a substantially greater or smaller angle relative to a longitudinal axis 20 (see FIG. 3). In this exemplary embodiment, the angled walls of the upper portion 14 will provide a narrower opening further within the patient (i.e., spaced from the incision) and a wider opening nearer the skin (i.e., the area adjacent to an incision). The opening through this portion can be similarly angled, which can thereby provide the surgeon with additional room to maneuver instruments and devices from outside the body and the device, yet minimize the size of the patient's incision, as will be described below relative to FIG. 3. Alternatively, the opening through the upper portion 14 can be generally cylindrical through its height.

The outer profile of the upper portion 14 further includes two sides 42, 44 that are spaced from each other on opposite sides of the device 10 and extend generally in the direction of the longitudinal axis 20. These sides 42, 44 can be relatively planar along their lengths, as shown, or can be curved, sloped, angled, or otherwise configured. The sides 42, 44 can be generally parallel to each other and extend in the direction of the longitudinal axis 20. In one embodiment, each of the sides 42, 44 generally defines one edge surface of the upper portion 14 such that no flanges or other portions extend outwardly from these sides. However, it is contemplated that additional flanges or features can extend outwardly from sides 42, 44, if desired.

The upper portion 14 further includes two surfaces 36, 38 that extend between opposite ends of the sides 42, 44. Surfaces 36, 38 are shown as being concave or curved toward the longitudinal axis 20 (and toward each other), which can advantageously provide gripping surfaces for the user to grasp and compress the device, as will be described below. Alternatively, the surfaces 36, 38 can be angled, linear, curved in a convex manner, or otherwise configured to allow for manipulation of the device.

A central port or opening 22 is illustrated as being a generally circular or cylindrical opening that extends through the entire height of the device 10 in the direction of the longitudinal axis 20. That is, opening 22 extends through the lower portion 12 and upper portion 14 and has sides that are generally parallel to the longitudinal axis 20. However, opening 22 can be tapered or otherwise shaped along its length to accommodate certain surgical instruments, for example. That is, while the figures illustrate a central opening that is generally cylindrical (i.e., having a constant diameter and shape through the height of the device 10), the shape and size of the opening 22 can instead vary along its height within lower portion 12 and/or upper portion 14, such as is described above relative to each of these portions.

Figure 3:
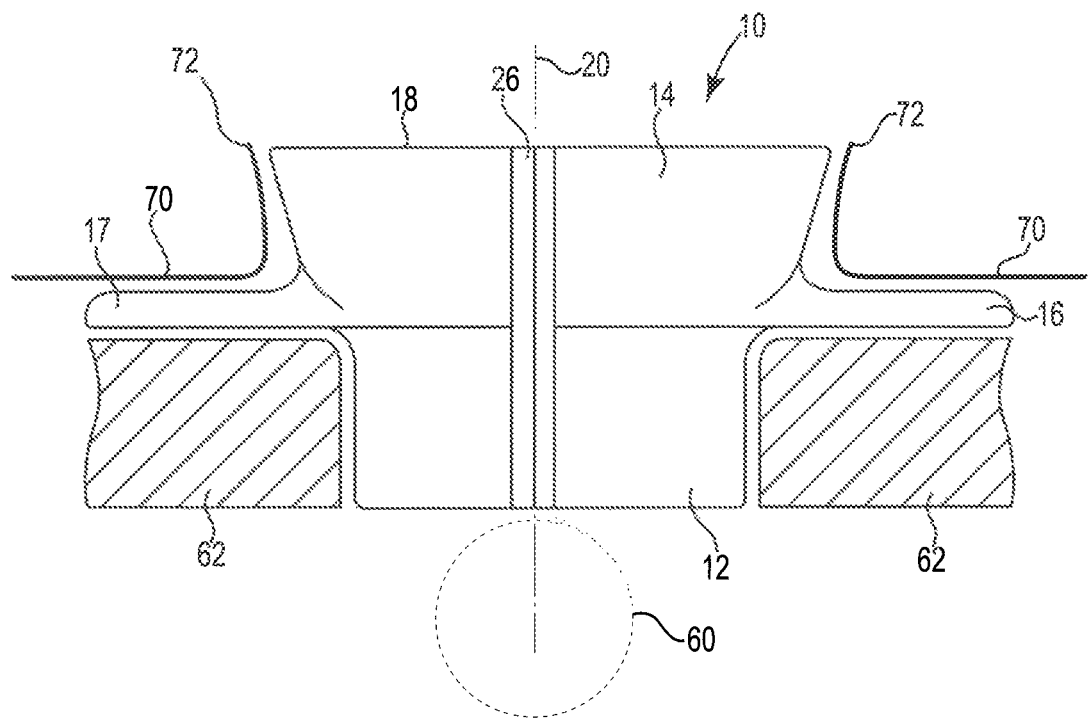
FIG. 3 is a side view of the device of FIG. 1 as positioned relative to a schematic representation of an aorta.

In one particular exemplary use of the device 10, the device is used for access to an aorta 60, as is illustrated schematically in FIG. 3. As illustrated, device 10 is positioned so that the flanges 16, 17 are positioned under a layer of skin 70 and so that the upper portion 14 is adjacent to edges 72 of the incision (i.e., within the opening created by the incision). The lower portion 12 of this embodiment can be generally cylindrical, or can have an outer surface that is more elliptical, square, or another shape that will provide the size and shape of opening desired for surgical access to the aorta, for example. In addition, the lower portion 12 should have a height that is sufficient to extend from the upper portion 14 and through any layers of subcutaneous fat 62 so that the surgeon can thereby access the desired area beyond the layers of fat. However, the lower portion 12 should not be so tall that it causes interference with any organs within the patient.

Further, in this exemplary use of the device, the opening in upper portion 14 can also be generally cylindrical, or can have an outer surface that is more elliptical, square, or another shape that will provide the desired access for the surgeon into the internal area of the patient. The upper portion 14 should have a height that is sufficient to extend from the lower portion 12 and flange portions 16, 17 to provide easy access to the opening 22 by the surgeon. In any case, the upper portion 14 is preferably provided with at least a slight outward taper, as shown. Further, the upper portion 14 includes a gap 26 that extends along at least a portion of the height of the device 10 to facilitate installation of the device 10 in the patient, as is described below.

Figure 4:
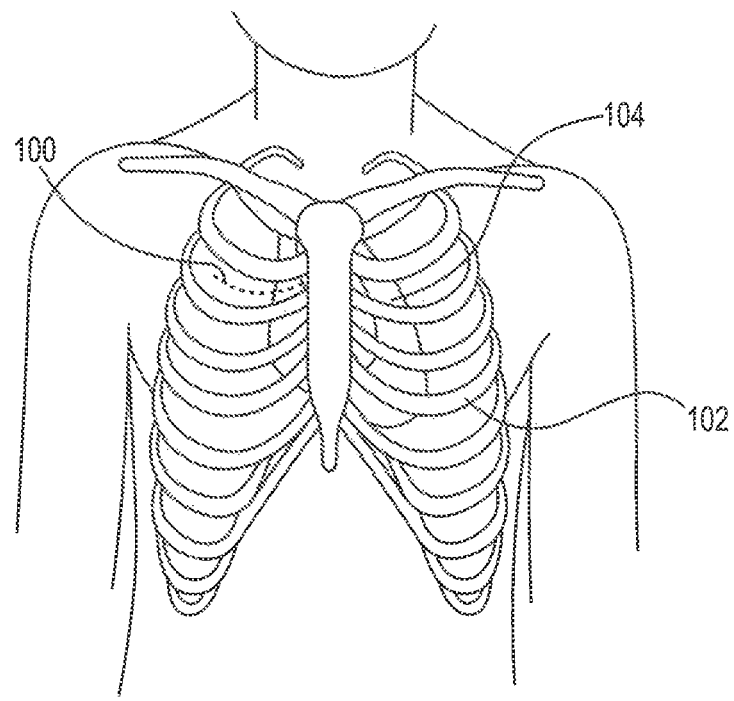
FIG. 4 is a front view of a chest area of a patient with an illustrated exemplary incision area that can provide access for placement of a device of the invention.

In accordance with the invention, device 10 is preferably made of plastic or another deformable, flexible material. In this way, device 10 can be temporarily reconfigured, such as by grasping the upper portion 14 at the concave surfaces 36, 38 with a thumb and forefinger, and squeezing or pressing these surfaces 36, 38 toward each other (e.g., as is illustrated by directional arrows 28, 30). This pressure on the device will cause the gap 26 to become smaller or to close, and with continued pressure, opposite sides 32, 34 of the gap 26 can come in contact with and/or pass by each other. Once the device 10 is deformed by an amount that is determined to be sufficient, it can be gently inserted into a gap or incision that has been made in the tissue of a patient, with the lower portion 12 being positioned furthest within the incision site, as is illustrated in FIG. 3. One exemplary location for an incision 100 is illustrated in FIG. 4, which illustrates the ribs 102 and heart 104 of a patient. In one embodiment, incision 100 can be approximately 2-3 inches in length and is made in the chest wall between the ribs to allow a surgeon to perform minimally invasive heart surgery. It may be necessary to move muscles or fat layers in order to properly insert the device 10 to allow the surgeon to be able to reach the desired area of the heart (e.g., the aorta). Alternatively, the incision can have a different length and/or may be made in a different area of the body than that described herein relative to FIG. 4.

Referring again to FIG. 3, the at least partially compressed device 10 is positioned relative to the edges 72 of the incision so that the flange portions 16, 17 are positioned in the area just below the skin 70, and then the device 10 can be released to allow it to expand back toward its original configuration. That is, the gap 26 can return to its original size and/or configuration, unless the anatomy of the patient inhibits the complete expansion of the device 10 back to its original condition. In this way, a port or pathway to the area just below the device 10, such as the aorta, for example, will be opened. In one method of positioning this device 10, it can initially be inserted longitudinally within the incision (e.g., with one of the flanges 16, 17 entering the incision area first), and then rotated approximately 90 degrees or until the flange portions 16, 17 are seated under the incision tissue to anchor the device in position and prevent or minimize the possibility of the device 10 unintentionally moving outside the body. The opposite procedure can be used for removal of the device 10 from the patient, if desired.

The present invention has now been described with reference to at least one embodiment thereof. The contents of any patents or patent application cited herein are incorporated by reference in their entireties. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A surgical access device comprising:
   a lower portion comprising a central opening spaced from a lower portion outer wall;
   an upper portion adjacent to the lower portion and comprising a central opening spaced from an upper portion outer wall; and
   at least one flange portion extending outwardly from the upper and lower portions;
   wherein the central openings of the lower and upper portions combine to define a common longitudinal axis;
   and further wherein the lower and upper portions extend from one another along the longitudinal axis, including the lower portion terminating at and defining a lower end of the device and the upper portion terminating at and defining an upper end of the device opposite the lower end;
   and further wherein the at least one flange portion defines opposing lower and upper faces, the lower face facing, and longitudinally spaced from, the lower end, and the upper face facing, and longitudinally spaced from, the upper end;
   and further wherein the lower and upper portions combine to define opposing, first and second gap edges each extending to and between the lower and upper ends, the gap edges combining to define a gap extending from and open to the central opening of the lower and upper portions and through the lower and upper portion outer walls, the first and second gap edges having continuous, complimentary shapes configured such that the first gap edge slides over the second gap edge when the device is subjected to a compressive force, including along the upper portion;
   and further wherein the outer wall of the upper portion is radially spaced from the longitudinal axis by a thickness of the outer wall of the upper portion, and further wherein the outer wall of the upper portion comprises at least one gripping surface;
   and even further wherein the at least one gripping surface comprises a first concave curved gripping surface that is curved toward the longitudinal axis and extends from the upper face of the at least one flange portion to the upper end.

2. The device of claim 1, wherein the device is compressible to provide a compressed gap width that is smaller than a width of the gap when the device is not compressed.

3. The device of claim 2, wherein the device is self-expandable after compression to provide a gap width that is larger than the compressed gap width.

4. The device of claim 1, wherein the lower and upper portions are adjacent to each other along the longitudinal axis.

5. The device of claim 1, wherein each flange portion extends in a perpendicular direction relative to the longitudinal axis.

6. The device of claim 1, wherein the at least one flange portion comprises a first flange portion positioned on an opposite side of the device from a second flange portion and wherein the first flange portion extends in an opposite direction relative to the longitudinal axis than the direction that the second flange portion extends.

7. The device of claim 1, wherein the at least one gripping surface further comprises a second gripping surface having a concave curved surface, and wherein the first and second gripping surfaces are positioned on opposite sides of the longitudinal axis.

8. The device of claim 1, further comprising a common central opening comprising the central openings of the lower and upper portions, wherein the common central opening is cylindrical.

9. The device of claim 1 wherein the common longitudinal axis is entirely linear from the lower end to the upper end.

10. The device of claim 1, wherein the at least one flange portion includes opposing, first and second flanges extending in opposite directions relative to the longitudinal axis, the first and second flanges combining to define a maximum transverse dimension of the device in a direction perpendicular to the longitudinal axis.

* * * * *